(12) United States Patent
Capperrune

(10) Patent No.: US 6,499,436 B1
(45) Date of Patent: Dec. 31, 2002

(54) PORTABLE RESTRAINT AND CONFINEMENT DEVICE

(76) Inventor: Dan Capperrune, P.O. Box 168, Bradford, IL (US) 61421

( * ) Notice: Subject to any disclaimer, the term of this patent is extended or adjusted under 35 U.S.C. 154(b) by 0 days.

(21) Appl. No.: 09/154,916

(22) Filed: Sep. 17, 1998

Related U.S. Application Data

(62) Division of application No. 08/818,909, filed on Mar. 17, 1997.

(51) Int. Cl.$^7$ ................................................ A01K 29/00
(52) U.S. Cl. ....................................................... 119/792
(58) Field of Search ................................ 119/792, 753, 119/756; 70/16, 18

(56) References Cited

U.S. PATENT DOCUMENTS

| | | | |
|---|---|---|---|
| 450,633 A | 4/1891 | Motter | |
| 3,007,331 A | 11/1961 | Irwin | |
| 3,426,559 A | 2/1969 | Schuback et al. | |
| 3,716,029 A | 2/1973 | Pillsbury, Jr. | |
| 4,147,129 A | 4/1979 | Ruplen | |
| 4,173,974 A | 11/1979 | Belliveau | |
| 4,316,433 A | * 2/1982 | Hebert | 119/158 |
| 4,693,212 A | * 9/1987 | Black | 119/103 |
| 5,085,174 A | 2/1992 | Etkin | |
| 5,092,592 A | 3/1992 | Fitzmaurice | |
| 5,103,769 A | 4/1992 | Macintosh | |
| 5,581,853 A | 12/1996 | Miller et al. | |

FOREIGN PATENT DOCUMENTS

| | | |
|---|---|---|
| SU | 1335274 | 9/1987 |
| SU | 1443877 | 12/1988 |

OTHER PUBLICATIONS

Foster Smith (1997) Scrub–a–Dub Dog.
Cabelas (Spring, 1997) Roll–a–Table.

* cited by examiner

Primary Examiner—Nicholas D. Lucchesi
(74) Attorney, Agent, or Firm—Stout, Uxa, Buyan & Mullins, LLP; Frank J. Uxa

(57) ABSTRACT

A portable restraint and confinement device for confining an animal within a fixed boundary. The device includes a base panel which has an outer perimeter defining a fixed boundary. A securement strap is attached at one end to the center of the base panel and at the other end to an attachment device. The attachment device is configured for connecting to a harness, collar or other holding device secured to the animal wherein the animal is confined within the fixed boundary by the securement strap. Alternate configurations of base panel are disclosed for improving portability as well as for use in specific environments and locations. An embodiment is disclosed for use in restraining and confining humans to within a fixed boundary.

2 Claims, 4 Drawing Sheets

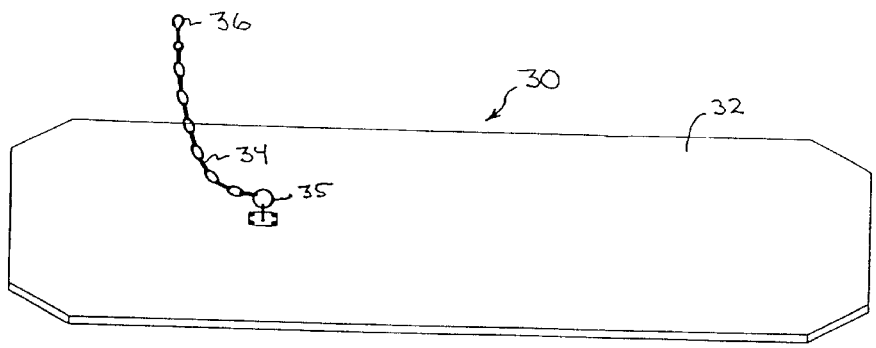
Fig. 2
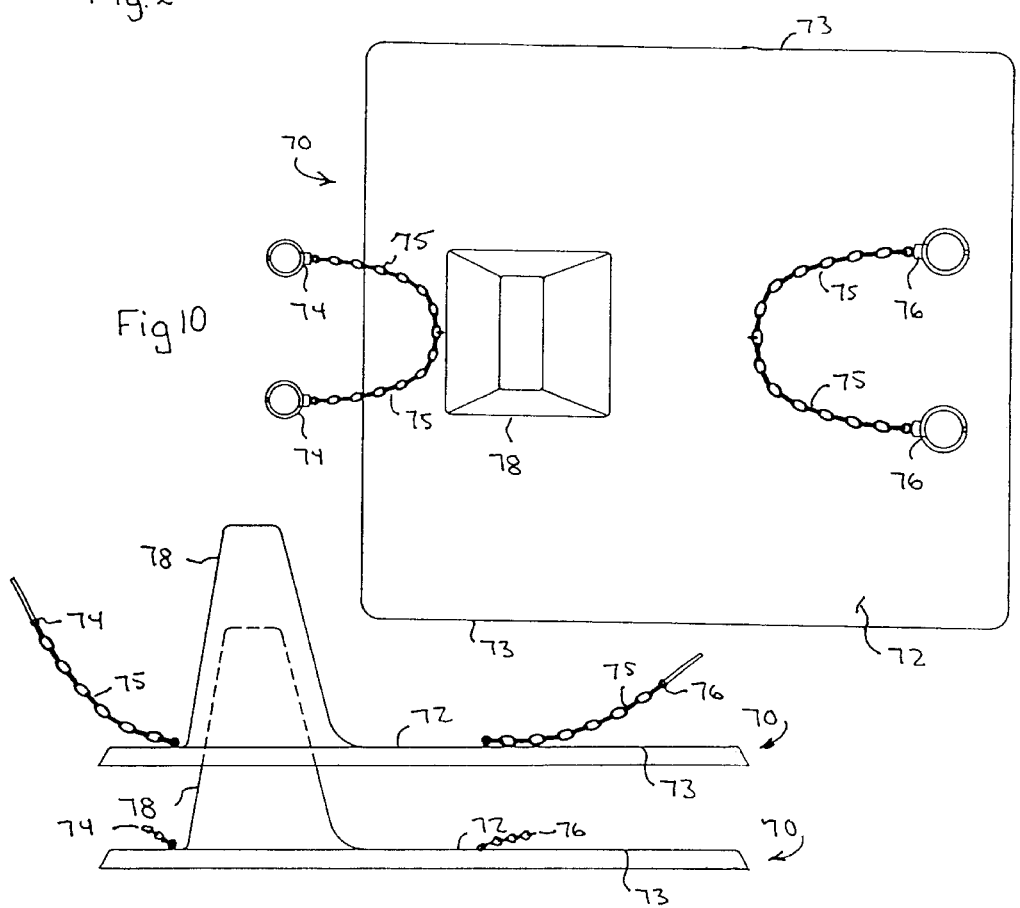
Fig 10
Fig. 11

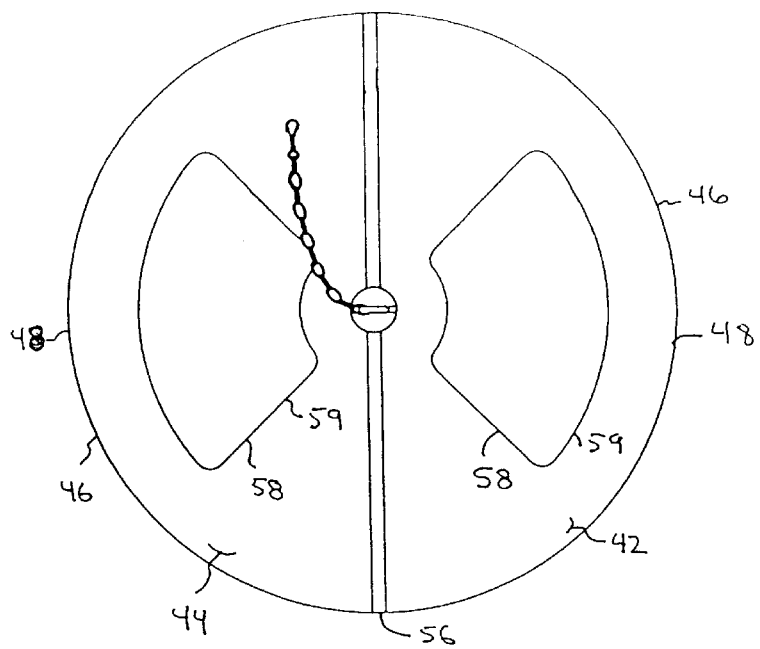
Fig. 6
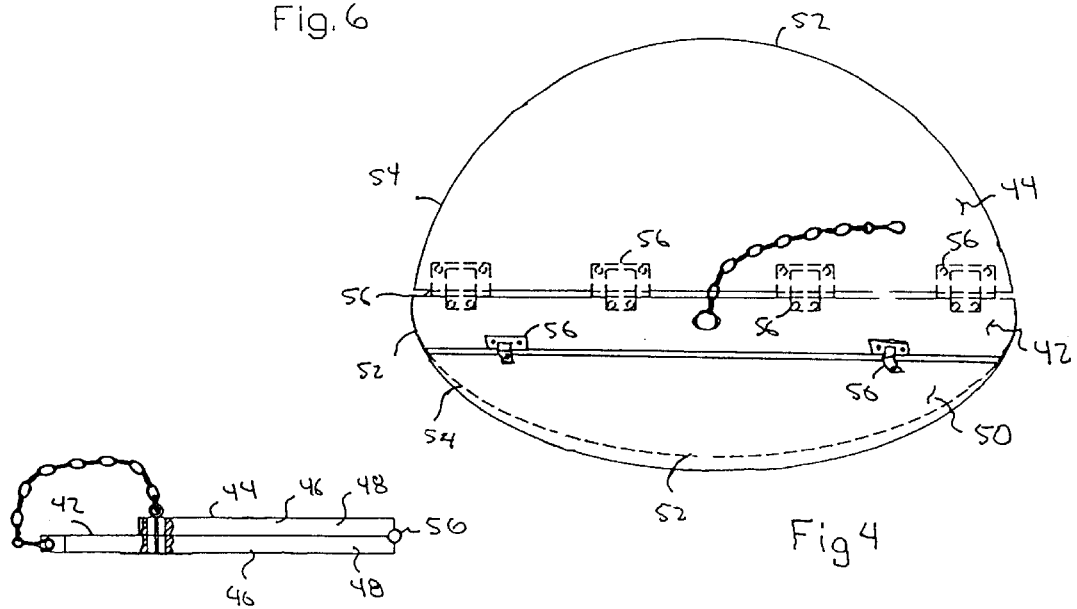
Fig 4
Fig. 5

PORTABLE RESTRAINT AND CONFINEMENT DEVICE

This is a division of application Ser. No. 08/818,909 filed Mar. 17, 1997, the contents of which are expressly incorporated herein by reference.

FIELD OF THE INVENTION

This invention relates generally to restraining and confining devices and more particularly, to a portable physical restraint and confinement device for humans and animals.

BACKGROUND OF THE INVENTION

The need for devices which restrain and confine animals, including humans, to within a specified boundary has been long known. When used with humans, such restraint and confinement devices are often used for punishment, protection, and to prevent escape. When used for animals, these devices are typically used for behavior training, to prevent escape, to limit mobility within a residence or business, and as an exercise device.

Jail cells, cages, and similar enclosures have been used for hundreds of years to confine humans. Other devices such as a heavy ball and chain have also been used. These devices, while effective at confining humans have numerous disadvantages. In particular, none of these devices are conveniently portable.

In fact, most conventional portable confinement devices available for use with humans are solely restraint devices. These devices, including hand cuffs or other shackle type devices, merely restrain mobility. However, even if a person has their hands restrained and their feet or legs restrained, the person may still be able to roll, hop or otherwise move, escape or cause other problems. In addition, the person retains sufficient mobility to injure another person as well as themselves.

The use of multiple shackle-type devices with a confining chain or chain gang type system has also been used for the restraint and confinement of large groups of persons. However, these devices have similar disadvantages to the restraint devices previously described. In addition, these systems commonly connect a potentially large number of people who can commonly see and communicate with each other as well as their environment. This communication and potential for common action is particularly dangerous because a number of the commonly confined people could act in unison. Also, a chain gain makes it very difficult to isolate individuals. This limits their application to generally low-risk type environments and situations. Thus, there is a need for a portable confinement device which safely confines a person within a fixed boundary. There is also a need for such a device which can safely confine a large number of people in any situation, such as during riot control.

Cages, fenced areas and tether systems have commonly been used to confine animals over the years. These systems are effective at restraining and confining animals, as well as humans, but have also numerous disadvantages. In particular, most of these devices are not generally portable. In addition, these devices can be dangerous as well as cruel to the subject animal.

More recently, portable animal enclosures have become available for use with domestic animals such as household pets. These enclosures or small cages are commonly used when travelling or otherwise transporting the pet. However, these portable enclosures are typically very small and light-weight so as to only be usable with very small pet. In addition, the devices are often considered cruel if used for more than immediate transportation or for other than short durations.

Other types of portable restraining devices have also recently become available for use with household pets. These devices are designed to provide a confined area in which the pet can freely move. In addition, some of these device contain feeding and toilet areas. However, these devices generally require a large flat rectangular floor area on which they must be placed.

For example, U.S. Pat. No. 3,716,029, issued to Pillsbury discloses an animal exercising device. This device comprises a platform of rigid sheets arranged to lie flat or to overlie one another. A housing is mounted on the platform which encloses an electric motor arranged to power a shaft and attached cantilever structure. A leash is attached at one end to the cantilever and to the animal at the other end. When the motor is energized, the animal is forced to exercise in a circular pattern around the shaft.

U.S. Pat. No. 4,147,129, issued to Ruplen, discloses an animal platform comprising a number of overlapping platform pieces pivoted together to form a main platform. A sleeping station having a fixed sleeping blanket and a removable toilet station are also provided to fit within the platform boundary. A centrally located tether is used to restrain the animal to within the platform boundary.

U.S. Pat. No. 5,085,174, issued to Etkin, discloses a pet trainer for the toilet training of small household pets. The trainer comprises a rectangular flat panel surrounded by a raised peripheral lip. The panel is sized to receive a sheet of unfolded newspaper. The pet is retained within the peripheral lip of the panel by a centrally located tether which is connected to the collar of the pet.

Thus, there is a need for a confinement device which can safely confine an animal, including a human, within a fixed boundary and is very portable. There is also a need for such a device which is useable in a number of differing locations. There is also a need for such a device which is simple to use and inexpensive to manufacture.

SUMMARY

The present invention satisfies the need for a restraint and confinement device which can safely confine an animal, including a human, within a fixed boundary by providing a device having a base which defines the fixed boundary and at least one securement device for retaining the animal, including the human, within the fixed boundary. By confining the animal within the periphery of the base, the animal's weight helps to retain the base of the confinement device in place. By adjusting the size and shape of the base, the confinement device of the present invention is adaptable for use at a number of different locations, as well as with differing types and sizes of animals.

The present invention in generally directed to a portable restraint and confinement device for confining an animal within a fixed boundary. The device comprises a first base panel which has an outer perimeter defining a fixed boundary. A first end of a securement strap is attached to a junction point secured in the center of the first base panel while the second end remains extendable outwardly a short distance from the junction point. An attachment device is connected to the second end of the securement strap and is secured to the animal or to a harness on the animal. In this way, the animal is confined within the fixed boundary by the securement strap.

In another broad aspect of the present invention, the portable restraint and confinement device includes a second base panel which is removably connected to the first base panel. A second fixed boundary is formed by S a second outer perimeter defined by the combination of the first base panel and the removably connected second base panel. The animal, restrained by the securement strap is now confined within the second fixed boundary. Alternatively, a third base panel may be removably connected to the first base panel opposite the second base panel to form a third outer perimeter. In this way, a third fixed boundary may be created within a third outer perimeter defined by the overall outer perimeter of the first, second and third base panels. Thus, any number of additional base panels may be removably added to create an increasingly larger outer perimeter and thus, larger fixed outer boundary area for confining the animal.

In yet another aspect of the present invention, the portable confinement device includes a base panel made from a flexible material. The flexible material may be rolled up to provide ease of portability as well as preventing injury or damage when struck. In addition, the flexible base panel provides a non-wear surface for the securement strap and a generally softer surface for the confined animal.

In yet another broad aspect of the present invention, the portable confinement device is adapted for restraining an animal within a specific location such as a conventional bathtub or other specifically configured location. The device comprises a base panel which has an outer perimeter generally configured to be placed within a conventional bathtub or other specifically shaped location. The base panel is shaped such that it easily fits within a bathtub but is not easily moved once placed. A securement strap is attached to a junction on the base panel at a first end. The non-rigid securement strap is generally extendable outwardly from the junction on the base panel. An attachment device is connected to the second end of the securement strap and allows for attachment of the securement strap to a harness or collar on the animal. Thus, the base panel fits within the bathtub and the animal is confined within the bathtub by the securement strap.

In an alternative embodiment, the portable restraint and confinement device of the present invention is adapted for confining a person within a fixed boundary. The device comprises a base panel with an outer perimeter which generally defines the fixed boundary. A pair of wrist restraining devices for removable connection with the wrists or arms of a person are attached to the base panel. The wrist restraining devices restrain and confine the person within the fixed boundary.

In yet another aspect of the present invention, the restraining and confining device is adapted to include a pair of leg restraining devices attached to the base panel in conjunction with and spaced apart from the pair of wrist restraining devices. In this aspect of the invention, a pair of leg restraining devices includes a pair of leg shackles and the wrist or arm restraining devices includes a pair of handcuffs. In this way, the person is confined by having both their arms and legs restrained, thus preventing them from injuring themselves as well as others. The base panel, which generally supports the person, comprises a flat surface made in a generally hollow fashion such that a number of these devices may be stackable while occupying a minimum of space.

The invention, together with additional features and advantages thereof, which was only summarized in the foregoing passages will become more apparent to those of skill in the art upon reading the description of the preferred embodiments, which follows in this specification, taken together with the following drawings.

BRIEF DESCRIPTION OF THE DRAWINGS

FIG. 2 is a perspective view of an alternative embodiment of a portable restraint and confinement device according to the present invention shown configured for use in a conventional bathtub.

FIG. 4 is a perspective view of the portable restraint and confinement device of FIG. 3 shown having multiple folding base panels.

FIG. 5 is a side view of the portable restraint and confinement device illustrated in FIG. 4 shown in a folded position.

FIG. 6 is a perspective view of the portable restraint and confinement device of FIG. 3 shown incorporating a feeding area and a toilet area into the base panels.

FIG. 10 is a perspective view of the portable restraint and confinement device of FIG. 9 shown incorporating a back support.

FIG. 11 is a cross sectional view of two portable restraint and confinement devices as shown in FIG. 10, taken along line 11—11.

DESCRIPTION OF THE PREFERRED EMBODIMENTS

Figure 1:
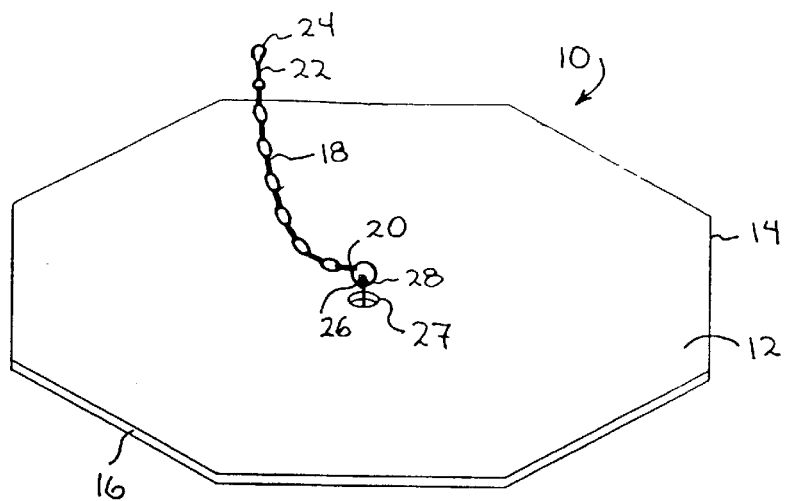
FIG. 1 is a perspective view of an embodiment of a portable restraint and confinement device according to the principles of the present invention.
Figure 3:
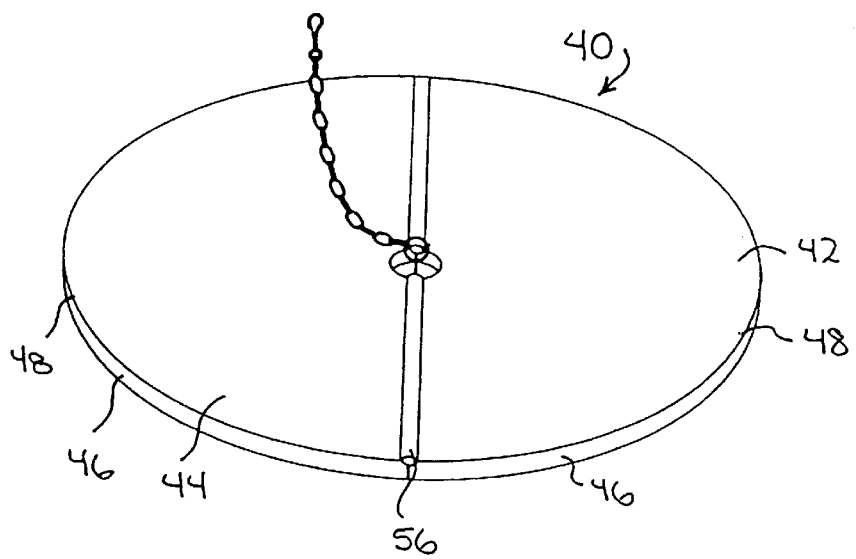
FIG. 3 is a perspective view of the portable restraint and confinement device of FIG. 1 shown having a foldable base panel.

Accordingly, a preferred embodiment of a portable restraint and confinement device 10 formed in accordance with the present invention is shown in FIG. 1. The portable restraint and confinement device 10 includes a first base panel 12 which has an outer perimeter 14 that defines a first fixed boundary 16. A securement strap 18 is attached to the first base panel 12 at a first end 20 and extends outwardly from the base panel 12 to a second end 22. An attachment device 24 is connected to the second end 22 and is used for attaching the securement strap 18 to an animal or a harness on the animal (not shown).

For purposes of this invention, an animal may include both domestic as well as wild animals. The term animal may also include humans. However, in this embodiment, the portable restraint and confinement device 10 is preferably used with an animal such as a household pet or otherwise domesticated animal. The harness includes any device which allows a secure attachment to the animal and which is unremovable by the animal. The harness may include, for example, and not to be limited hereto, a body harness, a collar, a choker, hand-cuffs, leg shackles, and the like.

The first base panel 12 may be any flat panel or similar structure which is able to support an animal while resisting tearing, abrasion and other abuses common with confined animals. The base panel 12 is configured to lie relatively flat on the ground or on any other supporting surface. Thus, the first base panel 12 is preferably made from a flat structural material such as a plywood, plastic, metal or even a rubber. The first base panel 12 may also be made from a grated or otherwise open metal, plastic or rubber structure such that it may be easily cleaned, transported, repaired and allows passthrough in the event the animal relieves itself. Additional advantages to a grated structure, include being lightweight and also allowing easy securement to the ground or other supporting structure.

In a preferred embodiment, the first base panel 12 includes a generally centrally disposed junction point 26 for attaching the first end 20 of the securement strap 18. The junction point 26 which may be a metal or otherwise structural loop, clip, swivel bearing or any other device for attaching a chain or other securement strap to a panel, may pass through a hole 27 in the base panel 12. In this way, the junction point 26 generally includes a larger bottom portion or base member than the diameter of the hole 27 in the base panel 12. It is thus very important that the material and structure of the first base panel 12 surrounding the hole 27 and/or junction point 26 be sufficiently strong and tough to prevent tearout of the junction point 26 or the securement strap 18. Alternatively, the junction point 26, or even the first end 20 may be fastened directly to the first base panel 12 at the attachment point 26. In this way, the securement strap 18 may be bolted, screwed, adhered, molded, riveted or welded to the base panel 12. However, any means or method of attaching the first end 20 of the securement strap 18 to the first base panel 12 may be used.

The securement strap 18 which may be a conventional chain, flexible metal rope or any other flexible material capable of restraining the animal without being severed, damaged or injuring the animal, is preferably sized such that the animal must remain within the first fixed boundary 16. Thus, if the securement strap 18 is attached to a collar or the neck of the animal, the securement strap 18 should be of sufficient length to. prevent either the front or rear legs of the animal from going beyond the first fixed boundary 16, while allowing the animal maximum freedom within the fixed boundary 16. However, in many circumstances, it may be preferable to only confine the animal's front legs to within the fixed boundary 16. The securement strap 18 is thus typically shorter than the radius of the first base panel 12.

The securement strap 18 is thus typically made from any material which is flexible and yet strong enough to resist the pulling, gnawing, chewing or other abuses which may occur when confining an animal. Preferably, the securement strap 18 may be a lightweight chain. However, a flexible and elastic corded material such as a toughened rubber may be used. The securement strap 18 may also be made to be of variable or adjustable length such as to fit various sizes and types of animals. Thus, the securement strap 18 may be made from links as other similar type connectable lengths of material.

The attachment device 24 is attached to the second end 22 of the securement strap 18. The attachment device 24 allows for connection with a second securement device such as a collar which is attached to the animal as previously discussed. Depending upon the animal being confined, the attachment device 24 may be a simple spring clip, or alternatively, a more sophisticated device such as a screw clamp requiring the use of special tools. The attachment device 24 may include a swivel, a hub or other rotating-type device 28 to prevent twisting or winding of the securement strap 18. In a similar fashion, the first end 20 may be attached at the junction point 26 using a similar rotating device or swivel.

Referring now to FIG. 2, a modified embodiment of the portable restraint and confinement device of FIG. 1 will be described. In this embodiment, the portable restraint and confinement device 30 is similar to that previously described but utilizes a base panel 32 that may be shaped to fit within a specified location. In the embodiment shown, the base panel 32 is specifically configured to fit within a conventional bathtub for use with washing or otherwise confining an animal such as a household pet. However, the base panel 32 may be sized and configured for placement in most any location or situation, such as the bed of a pick-up truck, for example. Alternatively, the base panel 32 may be made from a modifiable material such as plastic or a sheet of rubber which can be cut or otherwise configured as desired. A rubber base panel 32 is preferred since it is non-marking and naturally adheres to the bathtub and may also be folded or rolled for enhanced portability.

A securement strap 34 is attached to the base panel 32 as previously described. This may include the use of a junction point 35 with or without an opening (not shown). However, in this embodiment, the securement strap 34 is preferably made from a non-corrodible material. In this way, the securement strap will not scratch or otherwise damage the supporting bathtub and will not corrode. The securement strap 34 may be attached at any location on the base panel 32 which confines the animal within the bathtub. Alternatively, the securement strap 34 may be attached anywhere on the base panel 32 according to the desired application and animal type and size. An attachment device 36 may be attached to the distal end of the securement strap 34 as previously described.

Referring now to FIGS. 3–6, s second modified embodiment of the portable restraint and confinement device of FIG. 1 will be described. In this embodiment, the portable restraint and confinement device 40 is similar to those previously described but incorporates a first base panel 42 and a second base panel 44. The second base panel 44 is preferably removably connected to the first base panel such that the first base panel 42 and the second base panel 44 combine to form a second outer perimeter 46 defining a second fixed boundary 48. In this embodiment, the portable restraint and confinement device 40 is configured as described in the previously discussed embodiments but improves portability by reducing the overall size of each base panel 42 and 44.

In a similar fashion, as can be seen in FIGS. 4 and 5, a third base panel 50 may be removably connected to the first base panel 42 such that the first, second and third base panels 42, 44 and 50 combine forming a third outer perimeter 52 which defines a third fixed boundary 54. In this way, portability of the portable restraint and confinement device 40 can advantageously be improved by reducing the individual size of each of the base panels 42, 44 and 50 yet increasing the overall size of the bounded area or third fixed boundary 54. The overall fixed boundary can also be increased in size by adding additional base panels. In this way, a user with a small pet or other animal may begin with a single base panel 42 and as the pet grows in size, enlarge the fixed boundary by increasing the number of additional base panels as well as the length of the securement strap.

A removable connection 56 between each of the connected base panels 42, 44 and 50 preferably comprises a removable hinge device 56. This removable hinge device 56 may include conventional hinges which are removable when oriented at a particular angle. Thus, when the portable restraint and confinement device 40 is folded for storage or portability, the base panels 42, 44 and 50 may be individually removed when appropriately folded. However, alternative hinge or other removable connection devices may also be used. Such devices may include a strip of flexible rubber or other elastic material, links of chain, or any other hinge type or removable connection type devices as are commonly used to hingably or otherwise removably connect two adjoining panels.

As shown in FIG. 6, either one or both of the first and second panels 42 and 44 may be provided with a feeding, sleeping, toilet or other type of device 58 to enhance the cleanliness and comfort for the animal. The comfort, cleanliness or other device 58 may be made integral within the associated base panel or may be supplied as a separate tray or pad. If supplied as a separate piece, it is preferred that the comfort and cleanliness device 58 be bolted, strapped or otherwise secured to each of the base panels 42 and 44. In a preferred embodiment, a feeding dish 58 is set within an integrally formed recess 59 within the first base panel 42 and a toilet pan 58 is set within an integrally formed recess within 59 the second base panel 44.

Figure 7:
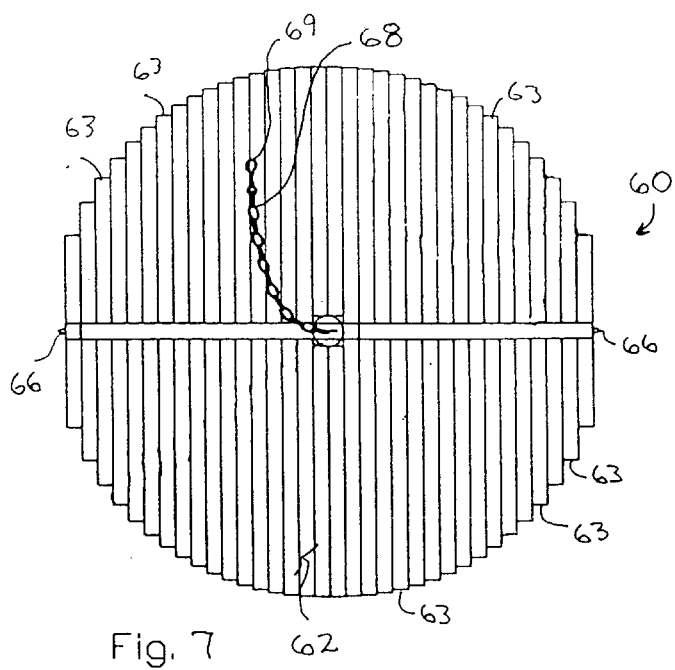
FIG. 7 is a perspective view of the portable restraint and confinement device of FIG. 1 shown having a flexible base panel.
Figure 8:
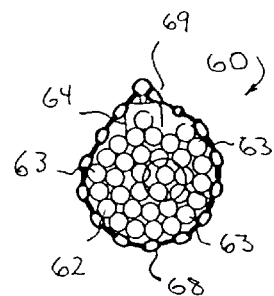
FIG. 8 is a side view of the portable restraint and confinement device of FIG. 7 shown in a rolled up position.

A fourth preferred embodiment of a portable restraint and confinement device 60 according to the present invention is shown in FIG. 7. In this embodiment, the portable restraint and confinement device 60 is similar to the embodiments as previously described but also includes a base panel 62 which is flexible and may be made from a multitude of individual elongated bars 63 or other elements which are hingably connected to each other and can be rolled relative to each other. In this fashion, the base panel 62 may be flexible in one direction but remain rigid in the opposing direction. A locking bar 64 is provided for securing the base panel 62 in the extended and rigid position. In this fashion, the base panel 62 may be rolled up as shown in FIG. 8 for portability yet unrolled and remain rigid when used.

The locking bar 64 which may be a single flat piece of rigid material is generally provided with locking tabs or ends 66 which attach to the outer edge of the base panel 62. In this way, the base panel 62 is prevented from flexing, bending or otherwise being rolled. A securement strap 68 and an attachment device 69 are attached to the base panel 62 as described in previous embodiments. However, the securement strap 68 may also be attached to a single or plurality of the elongated bars 63.

Alternatively, the base panel 62 may be made from a flexible material such as a sheet of rubber or flexible plastic. In this way, the base panel 62 may provide a soft durable surface for the confined animal as well as simplifying handling and storage requirements. In this fashion, the securement strap is attached to the base panel 62 as described for the previous embodiments.

Figure 9:
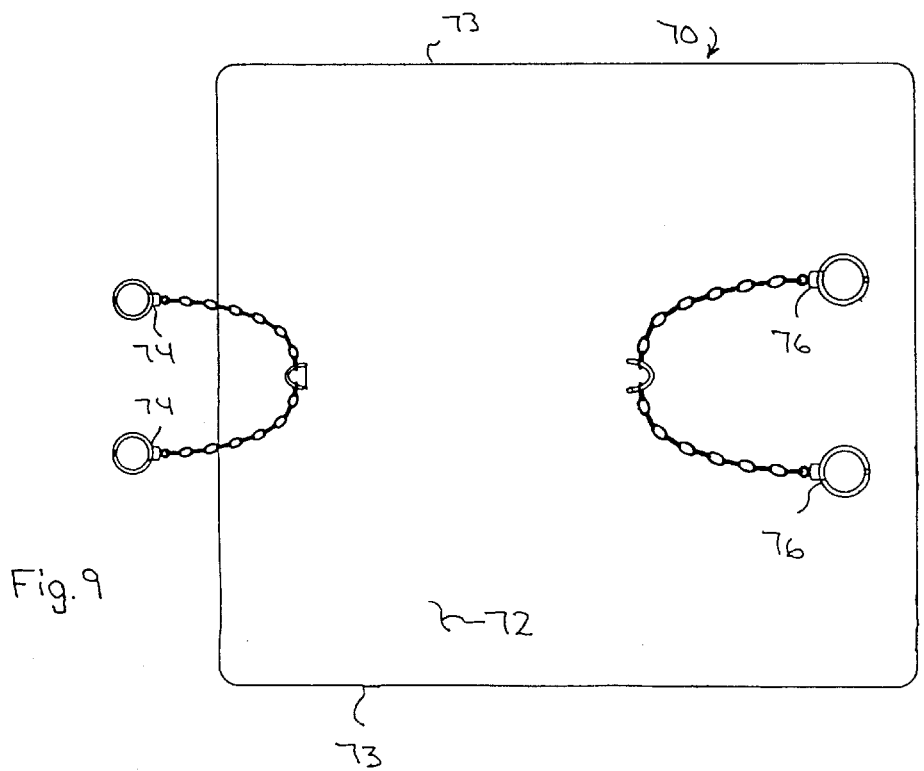
FIG. 9 is a perspective view of an alternative embodiment of a portable restraint and confinement device according to the present invention shown configured for use with humans.

Referring now to FIGS. 9–11, an alternative embodiment of a portable restraint and confinement device 70 according to the principles of the present invention will be described. In this embodiment, the portable restraint and confinement device 70 is advantageously configured for use with humans. A base panel 72 comprised of a generally flat rigid material is configured for placement on the ground or other supporting surface (not shown). The base panel 72 may be made from a rubber, plastic or other soft material and alternatively, may include a lining or pad to increase comfort and minimize the potential for injuries.

A pair of wrist restraining devices 74 may be attached to the base panel 72 such that a person (not shown) may be restrained and confined to within a fixed boundary 73 defined by the base panel 72. In a preferred embodiment, the wrist restraining devices 74 comprise a pair of handcuffs which are attached to the main body 72. This attachment may include a clip, bolted fastening, rivets, or any other method of attaching handcuffs or any other chain or cable type material to a planar body which cannot be broken loose without the aid of some form of a special tool or other device. The wrist restraining devices 74 may include linking chains 75.

A pair of leg restraining devices 76 may also be attached to the base panel 72. The leg restraining devices 76, similar to the wrist restraining devices 78 may include a linking cable or chain 75. The linking chain 75 allows movement of the limbs and may be sized according to securement or other requirements. In this fashion, a person may be secured to the base panel 72 by securing both the legs and the arms. Thus, the person is restrained from further movement outside of the fixed boundary 73. In this way, the person is prevented from injuring himself as well as others. Preferably, the leg restraining device 76 comprises leg or ankle shackles which are also attached to the base panel 72 apart from the wrist or arm restraining devices 74. However, any device for restraining the ankles or legs of a person may be used.

Referring now in particular to FIGS. 10 and 11, a back support 78 may be attached to the base panel 72. In this configuration, a person may be secured to the base panel 72 in a sitting position with their arms restrained to their sides or behind the back. In addition, the back support 78 provides additional structural integrity to the base panel 72. Preferably, the base panel 72 and the back support 78 are integral and form a generally hollow structure 72. In this way the portable restraint and confinement device 70 may be stackable. Thus, a large number of portable restraint and confinement devices 70 may be stacked for storage or for transportation to a remote location as needed. It is envisioned that the portable restraint and confinement device 70 may be stackable such that a large quantity can be carried on and dispensed from a small truck or from a special trailer designed specifically for carrying these devices.

While this invention has been described with respect of various specific examples and embodiments, it is to be understood that the invention is not limited thereto and that it can be variously practiced within the scope of the following claims.

What is claimed is:

1. A portable restraint and confinement device for restraining an animal comprising:

a flexible base panel comprising a plurality of elongated elements connected to each other and adapted to be rolled relative to each other;

a securement strap having a first end attached to said base panel and a second end which is extendable outwardly from said base panel; and an attachment device connected to said second end for attachment of said securement strap to said animal.

2. The portable restraint and confinement device of claim 1 wherein said plurality of elongated elements include elements of differing lengths.

\* \* \* \* \*